US012788794B2

(12) United States Patent
Richardson

(10) Patent No.: US 12,788,794 B2
(45) Date of Patent: Nov. 10, 2026

(54) COMPOSITION FOR TREATING PAIN AND METHOD OF USE THEREOF

(71) Applicant: Peggy Ann Richardson, San Dimas, CA (US)

(72) Inventor: Peggy Ann Richardson, San Dimas, CA (US)

( * ) Notice: Subject to any disclaimer, the term of this patent is extended or adjusted under 35 U.S.C. 154(b) by 639 days.

(21) Appl. No.: 18/295,178

(22) Filed: Apr. 3, 2023

(65) Prior Publication Data

US 2023/0405077 A1 Dec. 21, 2023

Related U.S. Application Data

(60) Provisional application No. 63/473,414, filed on May 31, 2022.

(51) Int. Cl.

| | |
|---|---|
| ***A61K 36/00*** | (2006.01) |
| ***A61K 9/00*** | (2006.01) |
| ***A61K 9/06*** | (2006.01) |
| ***A61K 31/05*** | (2006.01) |
| ***A61K 35/644*** | (2015.01) |
| ***A61K 36/22*** | (2006.01) |
| ***A61K 36/28*** | (2006.01) |
| ***A61K 36/534*** | (2006.01) |
| ***A61K 36/54*** | (2006.01) |
| ***A61K 36/61*** | (2006.01) |
| ***A61K 36/889*** | (2006.01) |

(52) U.S. Cl.

CPC .......... *A61K 36/889* (2013.01); *A61K 9/0014* (2013.01); *A61K 9/06* (2013.01); *A61K 31/05* (2013.01); *A61K 35/644* (2013.01); *A61K 36/22* (2013.01); *A61K 36/28* (2013.01); *A61K 36/534* (2013.01); *A61K 36/54* (2013.01); *A61K 36/61* (2013.01)

(58) Field of Classification Search

CPC .................................................... A61K 36/889

See application file for complete search history.

(56) References Cited

U.S. PATENT DOCUMENTS

2021/0060113 A1* 3/2021 Pomilla ................ A61K 36/534

FOREIGN PATENT DOCUMENTS

CN 110305738 A * 10/2019 ............. C11C 5/002

* cited by examiner

*Primary Examiner* — Qiuwen Mi

(74) *Attorney, Agent, or Firm* — Sheppard, Mullin, Richter & Hampton LLP; Nathan J. Lee

(57) ABSTRACT

The present disclosure relates generally to a composition comprising natural ingredients suitable for use in providing relief for various ailments, including muscle and joint pain, inflammation, and minor skin irritations. Such natural ingredients may be selected from a group consisting of: coconut oil, mango butter, white beeswax, menthol crystals, *arnica* oil, peppermint oil, *eucalyptus* oil, cinnamon oil, camphor, ginger oil, and frankincense.

8 Claims, 2 Drawing Sheets

COMPOSITION FOR TREATING PAIN AND METHOD OF USE THEREOF

CROSS REFERENCE TO RELATED APPLICATIONS

The present application claims priority to and benefits of U.S. Provisional Patent Application No. 63/473,414, filed on May 31, 2022. The entire contents of the above-identified application are incorporated herein by reference.

BACKGROUND

Field

The present invention relates to a composition comprising natural ingredients suitable for use in providing relief for various ailments, including muscle and joint pain, inflammation, and minor skin irritations.

Background

There are many over-the-counter products available for the relief of muscle and joint pain, inflammation, and minor skin irritations. Many of these products contain synthetic ingredients that can cause adverse reactions in some users. Additionally, some of these products are not environmentally friendly and may have adverse effects on the environment.

The present invention provides a composition comprising a combination of natural ingredients that are safe, effective, and environmentally friendly. The ingredients have been selected for their properties that make them effective in providing relief for various ailments.

SUMMARY

In one aspect, the present disclosure is directed to a composition comprising natural substances for treating pain. In one aspect, the present disclosure is directed to a device for administering such composition to a patient in need thereof.

The present disclosure, in one embodiment, provides a composition comprising one or more ingredients selected from a group consisting of coconut oil, mango butter, menthol, *arnica* oil, peppermint oil, *eucalyptus* oil, cinnamon oil, and camphor. The composition may further comprise beeswax. In one embodiment, the composition may be provided in a solid form.

The present disclosure, in one embodiment, provides a method of treating pain, comprising administering the aforementioned composition to a patient in need of the treatment. In one embodiment, the composition may be applied topically. In one embodiment, the composition may be applied on the area of pain, or on the area of muscle cramps and/or muscle spasms.

The present disclosure, in one embodiment, provides a method of producing the composition.

The present disclosure, in one embodiment, provides a device for packaging and/or administering the composition.

Figure 1:
FIG. 1 illustrates a device for applying a composition according to one embodiment.

It will be recognized that some or all of the figures are schematic representations for purpose of illustration.

DETAILED DESCRIPTION

Compositions

The present invention provides a composition comprising a combination of natural ingredients including two or more of coconut oil, mango butter, white beeswax, menthol crystals, *arnica* oil, peppermint oil, *eucalyptus* oil, cinnamon oil, camphor, ginger oil, and frankincense. Each of these ingredients has been carefully selected for their properties that make them effective in providing relief for various ailments. In some embodiments, the composition includes three or more, four or more, five or more, six or more, seven or more, or eight or more of coconut oil, mango butter, white beeswax, menthol crystals, *arnica* oil, peppermint oil, *eucalyptus* oil, cinnamon oil, camphor, ginger oil, and frankincense.

Coconut Oil

Coconut oil is a natural moisturizer that helps to keep the skin soft and supple. It also is known to have anti-inflammatory and analgesic properties that make it effective in reducing pain and inflammation. In some embodiments, the composition may include the coconut oil in an amount of from about 25% to about 40%, from about 28% to about 40%, from about 30% to about 40%, about 32% to about 40%, from about 25% to about 37%, from about 28% to about 37%, from about 30% to about 37%, from about 32% to about 37%, from about 25% to about 35%, from about 28% to about 35%, from about 30% to about 35%, or from about 32% to about 35%, wherein the percentage is by weight.

Mango Butter

Mango butter is a natural emollient that helps to soften and soothe the skin. It also is known to have anti-inflammatory properties that make it effective in reducing inflammation and pain. In some embodiments, the composition may include the mango butter in an amount of from about 20% to about 35%, from about 23% to about 35%, from about 25% to about 35%, from about 20% to about 32%, from about 23% to about 32%, from about 25% to about 32%, from about 20% to about 30%, from about 23% to about 30%, from about 25% to about 30%, from about 20% to about 28%, or from about 25% to about 28%, wherein the percentage is by weight.

White Beeswax

White beeswax is a natural emulsifier that helps to combine the ingredients in the composition. It is also known to have anti-inflammatory and antibacterial properties that make it effective in reducing inflammation and preventing infection. In some embodiments, the composition may include the whiter beeswax in an amount of from about 15% to about 30%, from about 18% to about 30%, from about 20% to about 30%, from about 15% to about 27%, from about 18% to about 27%, from about 20% to about 27%, from about 15% to about 25%, from about 18% to about 25%, from about 20% to about 25%, from about 15% to about 23%, or from about 20% to about 23%, wherein the percentage is by weight.

Menthol Crystals

Menthol crystals are a natural analgesic that provides a cooling sensation to the skin. It is also known to have anti-inflammatory properties that make it effective in reducing pain and inflammation. In some embodiments, the composition may include the menthol crystals in an amount of from about 1% to about 10%, from about 2% to about 10%, from about 4% to about 10%, from about 1% to about 8%, from about 2% to about 8%, from about 4% to about 8%, from about 1% to about 6%, from about 2% to about 6%, or from about 4% to about 6%, wherein the percentage is by weight.

*Arnica* Oil

*Arnica* oil is a natural anti-inflammatory and analgesic that is commonly used to relieve muscle and joint pain. In some embodiments, the composition may include the *arnica* oil in an amount of from about 0.1% to about 3%, from about 0.5% to about 3%, from about 1% to about 3%, from about 0.1% to about 2%, from about 0.5% to about 2%, or from about 1% to about 2%, wherein the percentage is by weight.

Peppermint Oil

Peppermint oil is a natural analgesic and anti-inflammatory that provides a cooling sensation to the skin. It also has antispasmodic properties that make it effective in reducing muscle spasms. In some embodiments, the composition may include the peppermint oil in an amount of from about 1% to about 10%, from about 2% to about 10%, from about 2% to about 10%, from about 2% to about 8%, from about 2% to about 6%, from about 3% to about 10%, from about 3% to about 8%, from about 3% to about 6%, or from about 3% to about 4%, wherein the percentage is by weight.

*Eucalyptus* Oil

*Eucalyptus* oil is a natural analgesic and anti-inflammatory that provides a cooling sensation to the skin. It also has antispasmodic properties that make it effective in reducing muscle spasms. In some embodiments, the composition may include the *eucalyptus* oil in an amount of from about 1% to about 10%, from about 2% to about 10%, from about 4% to about 10%, from about 1% to about 8%, from about 2% to about 8%, from about 4% to about 8%, from about 1% to about 6%, from about 2% to about 6%, or from about 4% to about 6%, wherein the percentage is by weight.

Cinnamon Oil

Cinnamon oil is a natural analgesic and anti-inflammatory that provides a warming sensation to the skin. It also has antiseptic properties that make it effective in preventing infection. In some embodiments, the composition may include the cinnamon oil in an amount of from about 1% to about 10%, from about 2% to about 10%, from about 2% to about 10%, from about 2% to about 8%, from about 2% to about 6%, from about 3% to about 10%, from about 3% to about 8%, from about 3% to about 6%, or from about 3% to about 4%, wherein the percentage is by weight.

Camphor

Camphor is a natural analgesic that provides a warming sensation to the skin. It also has anti-inflammatory properties that make it effective in reducing pain and inflammation. In some embodiments, the composition may include the camphor in an amount of from about 0.1% to about 3%, from about 0.5% to about 3%, from about 1% to about 3%, from about 0.1% to about 2%, from about 0.5% to about 2%, or from about 1% to about 2%, wherein the percentage is by weight.

Ginger Oil

In some embodiments, the composition may include ginger oil. In some embodiments, the composition may include the ginger oil in an amount of from about 1% to about 10%, from about 2% to about 10%, from about 4% to about 10%, from about 1% to about 8%, from about 2% to about 8%, from about 4% to about 8%, from about 1% to about 6%, from about 2% to about 6%, or from about 4% to about 6%, wherein the percentage is by weight.

Frankincense

Cinnamon oil is a natural analgesic and anti-inflammatory that provides a warming sensation to the skin. It also has antiseptic properties that make it effective in preventing infection. In some embodiments, the composition may include the cinnamon oil in an amount of from about 1% to about 10%, from about 2% to about 10%, from about 2% to about 10%, from about 2% to about 8%, from about 2% to about 6%, from about 3% to about 10%, from about 3% to about 8%, from about 3% to about 6%, or from about 3% to about 4%, wherein the percentage is by weight.

Other Ingredients

The composition may include any other pharmaceutically acceptable carrier or ingredients, to maintain or modify desired chemical or physical properties.

Method of Manufacturing

In some embodiments, the composition is formulated by combining the ingredients in a suitable ratio to achieve the desired properties. In one embodiment, the composition comprises coconut oil, 20-30% mango butter, 20-30% white beeswax, 3-5% menthol crystals, 1-5% *arnica* oil, 3-7% peppermint oil, 2-7% *eucalyptus* oil, 1-5% cinnamon oil, and 1-5% camphor, wherein the percentage is by weight.

The ingredients are melted together over low heat (about 76° F.), and then stirred until the mixture is homogenous. The mixture is then allowed to cool and solidify.

Use

The composition can be applied topically to the affected area as needed. The composition may be used to treat and/or providing relief for various ailments, including muscle and joint pain, inflammation, and minor skin irritations.

In some embodiments, the composition may be applied once, twice, three time or more to the affected area per day.

The composition has the advantage of being all-natural, safe, and effective. The ingredients have been carefully selected for their properties that make them effective in providing relief for various ailments. Additionally, the composition is environmentally friendly and does not have adverse effects on the environment.

Dosage Form/Kit

Figure 2:
FIG. 2 illustrates a device for applying a composition according to one embodiment.

Unlike many aroma oils previously provided for pain relief, the composition may be in a solid form, such that it is easier to apply to skin without dripping or accidental application to sensitive area (e.g. eyes). For example, the composition may be in a deodorant-type stick form, such as shown in FIGS. 1 and 2. The composition may have an elongated, stick shape. In some embodiments, the composition may be other forms, such as cream, gel, ointment, oil, or patch.

In some embodiments, a kit for applying the composition is provided. The kit may include a composition in a solid form, and a casing at least partially enclosing the composition. The kit may further include a cap, wherein when the cap is assembled with the casing, they completely enclose the composition. In some embodiments, the casing may include means to push the composition out of/into, or slide out/in to the casing, such that at least a portion of the composition protrudes out of the casing for administration.

In some embodiments, such kit may be used by steps of the following: 1) opening the cap; 2) making the composition (in a solid form) to protrude out of the casing; 3) applying the composition on a skin of the affected area.

Definition

As used in the present specification, the following words, phrases and symbols are generally intended to have the meanings as set forth below, except to the extent that the context in which they are used indicates otherwise.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A composition comprising:

30-50% w/w coconut oil, 20-30% w/w mango butter, 20-30% w/w white beeswax, 3-5% w/w menthol crystals, 1-5% w/arnica oil, 3-7% w/w peppermint oil, 2-7% w/w eucalyptus oil, 1-5% w/w cinnamon oil, and 1-5% w/w camphor.

2. The composition of claim 1, wherein the composition is in a solid form.

3. A kit for treating pain in a subject, comprising:

a composition in a solid form, the composition comprising:

30-50% w/w coconut oil, 20-30% w/w mango butter, 20-30% w/w white beeswax, 3-5% w/w menthol crystals, 1-5% w/arnica oil, 3-7% w/w peppermint oil, 2-7% w/w eucalyptus oil, 1-5% w/w cinnamon oil, and 1-5% w/w camphor; and a casing at least partially enclosing the composition.

4. The kit of claim 3, wherein the composition has an elongated shape.

5. The kit of claim 3, further comprising a cap.

6. A method of treating pain in a subject, administering the composition of claim 1 to the subject in need thereof.

7. The method of claim 6, wherein the composition is applied topically.

8. The method of claim 6, wherein the composition is in a solid form.

* * * * *